United States Patent
Narvaez Rincon et al.

(10) Patent No.: US 9,765,283 B2
(45) Date of Patent: Sep. 19, 2017

(54) REACTION SYSTEM FOR PRODUCING FATTY ALKYL ESTERS USING A LIQUID-FILM REACTOR OPERATED COUNTERCURRENTWISE

(71) Applicant: UNIVERSIDAD NACIONAL DE COLOMBIA, Bogota (CO)

(72) Inventors: Paulo Cesar Narvaez Rincon, Bogota (CO); Juan Guillermo Cadavid Estrada, Bogota (CO); Ruben Darío Godoy Silva, Bogota (CO); Gerardo Rodriguez Niño, Bogota (CO)

(73) Assignee: UNIVERSIDAD NACIONAL DE COLOMBIA, Bogota (CO)

( * ) Notice: Subject to any disclaimer, the term of this patent is extended or adjusted under 35 U.S.C. 154(b) by 0 days.

(21) Appl. No.: 14/764,335

(22) PCT Filed: Jan. 28, 2014

(86) PCT No.: PCT/IB2014/058603
§ 371 (c)(1),
(2) Date: Jul. 29, 2015

(87) PCT Pub. No.: WO2014/118697
PCT Pub. Date: Aug. 7, 2014

(65) Prior Publication Data
US 2015/0368587 A1    Dec. 24, 2015

(30) Foreign Application Priority Data
Jan. 29, 2013  (CO) .................................... 13016083

(51) Int. Cl.
*C11C 3/00*  (2006.01)
*C11C 3/02*  (2006.01)
(Continued)

(52) U.S. Cl.
CPC .................. *C11C 3/04* (2013.01); *B01J 8/025* (2013.01); *B01J 8/0278* (2013.01); *B01J 8/0292* (2013.01);
(Continued)

(58) Field of Classification Search
CPC ......... C07C 67/00; C07C 67/03; C07C 69/00; C07C 69/52; C11C 3/00; C11C 3/003;
(Continued)

(56) References Cited

FOREIGN PATENT DOCUMENTS

| CN | 2908494 Y | * | 6/2007 |
| CO | 5920053 | | 5/2008 |

(Continued)

OTHER PUBLICATIONS

Machine translation of CN 2908494 Y, published on Jun. 6, 2007.*
(Continued)

*Primary Examiner* — Natasha Young
(74) *Attorney, Agent, or Firm* — Birch, Stewart, Kolasch & Birch, LLP

(57) ABSTRACT

This invention discloses a reaction system for producing fatty-acid alkyl esters using liquid film reactors, with countercurrent flow scheme based on the alcoholysis of fats and oils. Reaction system comprises a descending film reactor using semi-structured packing for generating interfacial area. It is fed through the bottom with oil or fat, and with a mixture containing alcohol, glycerol and catalyst through an intermediate stage. Products are a mixture of fatty-acid alkyl esters, alcohol and catalyst and alcohol, glycerol and catalyst, exit via the top and the bottom of the reactor, respectively. Volumetric packing fraction is between 2% and 50%, reaction temperature from 25 to 180° C., molar ratio alcohol to oil between 3:1 and 10:1, and CH3OH, NaOH, KOH, or their mixtures (0.5% to 3% based on the oil mass flow rate).
(Continued)

Conversion and yield in a single reaction step are greater than 99.7% and 99.9%, respectively.

12 Claims, 5 Drawing Sheets

(51) Int. Cl.

| | | |
|---|---|---|
| *C11C 3/04* | (2006.01) | |
| *C11C 3/06* | (2006.01) | |
| *C11C 3/10* | (2006.01) | |
| *C07C 67/00* | (2006.01) | |
| *C07C 67/03* | (2006.01) | |
| *C07C 69/00* | (2006.01) | |
| *C07C 69/02* | (2006.01) | |
| *B01J 8/02* | (2006.01) | |
| *B01J 19/24* | (2006.01) | |
| *B01J 8/00* | (2006.01) | |
| *B01J 19/00* | (2006.01) | |
| *B01J 19/30* | (2006.01) | |

(52) U.S. Cl.
CPC ........... *B01J 19/2405* (2013.01); *C07C 67/03* (2013.01); *C11C 3/003* (2013.01); *C11C 3/06* (2013.01); *C11C 3/10* (2013.01); *B01J 2219/24* (2013.01)

(58) Field of Classification Search
CPC ..... C11C 3/04; C11C 3/06; C11C 3/10; C11C 3/02; B01J 8/00; B01J 8/02; B01J 8/0242; B01J 8/025; B01J 8/0278; B01J 8/0292; B01J 19/00; B01J 19/24; B01J 19/2405; B01J 2219/24
See application file for complete search history.

(56) References Cited

FOREIGN PATENT DOCUMENTS

DE          19908978 A1 *  9/2000  .............. C11C 3/003
WO     WO 2011/108270 A1 *  9/2011

OTHER PUBLICATIONS

Machine translation of DE 19908978 A1, published on Sep. 21, 2000.*
Machine translation of WO 2001/108270 A1, published on Sep. 9, 2011.*
Cadavid et al., "Biodiesel production in a counter-current reactive extraction column: Modelling, parametric identification and optimization", Chemical Engineering Journal, vol. 228 (2013) pp. 717-723.
Narvaez et al., "Continuous Methanolysis of Palm Oil Using a Liquid-Liquid Film Reactor", Journal of American Oil Chemists' Society, vol. 86, No. 4 (2009) pp. 343-352.
Narvaez et al., "Continuous Process for the Production of Fatty Acid Methyl Esters in a Falling Liquid-Liquid Film Reactor", 2nd Mercosur Congress of Chemical Engineering and 4th Mercosur Congress on Process System Engineering, 2005, retrieved online (May 22, 2014) URL http://www.slashdocs.com/mthhin/1040-proceso-continuo-esteres-metilicos.html.

* cited by examiner

REACTION SYSTEM FOR PRODUCING FATTY ALKYL ESTERS USING A LIQUID-FILM REACTOR OPERATED COUNTERCURRENTWISE

This application is the U. S. national phase of International Application No. PCT/IB2014/058603, now WO 2014/118697, filed 28 January which designated the U.S. and claims priority to CO13 016-083 filed 29 Jan. 2013, the entire contents of each applications are hereby incorporated by reference.

This invention consists of a reaction system for the production of fatty acid alkyl esters using packed bed reactors, particularly liquid film reactors, with a counter-current feed flow scheme that is based on the alcoholysis of oils and fats and, specifically, the methanolysis of palm and soya bean oils.

ANTECEDENTS TO THE INVENTION

The foundations of fatty acid alkyl ester production and, specifically, the production of methyl esters were developed in the 1940s and are described in a collection of patents by E. I. Du Pont and Colgate Palmolive (Van Gerpen, 2005). The processes that are most widely used worldwide employ homogeneous alkaline catalysts, especially sodium or potassium methoxides and hydroxides, due to their high catalytic activity and low cost (Freedman et al., 1986). However, the problems that are associated with the formation of soaps and gels, which complicate separation and reduce productivity, require the use of oils and fats with low free fatty acid (FFA) and water contents (Freedman et al., 1984; Ma and Hanna, 1999; Meher et al., 2006). This decreases the profit margin because the process is greatly affected by the raw material costs, which constitute between 70% and 95% of the production cost (Zhang et al., 2003).

To solve this problem, acid catalysts (Lotero, 2005), heterogeneous alkaline (Georgogianni et al., 2009), and enzymes (Li et al., 2007) have been used, as well as processes that employ co-solvents (Boocock, 2003) or whose operational temperature and pressure conditions are supercritical for the alcohol (Marulanda et al., 2010). Nonetheless, processes that employ homogeneous catalysts are most widely utilized for the production of biodiesel at the industrial scale.

Stirred-tank reactors are used in processes that involve alkaline catalysts that are soluble in alcohol to bring the reaction phases into contact, including the alcoholic phase, which is a solution of the catalysts in the alcohol, and the oily phase, which is initially formed by the oil or fat. Tubular reactors with an upstream static mixer are employed in other processes and under conditions of turbulent regime at Reynolds (Re) numbers greater than 2,300, although a Re number greater than 10,000 is recommended for safe applications to prevent segregation of the reacting phases inside of the reactor (Assmann, 1996).

The synergy between soap formation by the reaction between the catalyst and the free fatty acids and the stirring that is required to generate an interface area for the mass transfer generates emulsions and gels that prolong the residence times in the equipment downstream of the reactors. This synergy also complicates the separation stages, increases the product loss and the need for reprocessing, and decreases productivity (Freedman et al., 1986; Ma and Hanna, 1999; Meher et al., 2006; Demirbas and Karslioglu 2007). To solve this problem, Narváez and Sanchez (2008) proposed using a falling liquid film reactor that is operated co-current. This type of reactor is described in U.S. Pat. No. 3,992,156 and U.S. Pat. No. 3,758,404 and is used to remove impurities like sulphydric acid and organic acids from combustibles such as gasoline, Jet A, and kerosene. In this type of reactor, interfacial area is generated without dispersing one phase within the other, which reduces the time that is necessary for product separation in the alcoholysis of oils and fats and allows the separation to occur simultaneously with the reaction.

Because of the reversibility of the reaction, at least two reaction stages are generally required with an intermediate separation of the phases that are rich in fatty acid alkyl esters and glycerol to shift the reaction toward the products.

In this invention, the feeding scheme for the reagents and the reactor configuration shift the chemical equilibrium toward the products. This increases the yield toward fatty acid methyl esters and eliminates the need for the intermediate separation and the second reaction stage. These factors increase the productivity of the process.

DIVULGATION OF THE INVENTION

This invention is a reaction system for the production of fatty acid alkyl esters through counter-current alcoholysis and consists of the following parts:

a. A falling liquid film reactor (1)[1] that uses a packing to generate the interfacial area.

[1] The numbers in parentheses correspond to the labels in FIG. 1.

b. An oil or fat (10) supply current that feeds the bottom of the reactor (11).

c. A supply current of a mixture that contains alcohol, glycerol, and a catalyst (20) that can feed an intermediate stage of the reactor (21, 22, 23).

d. A second supply current of a mixture that contains alcohol, glycerol, and a catalyst (30) in different proportions than those in the mixture that is used in the first current (20). The second current can feed an intermediate stage of the reactor (31) or the top of the reactor (32).

e. An outlet for fatty acid alkyl esters, alcohol, and catalyst at the top of the reactor (40).

f. An outlet at the bottom of the reactor (50), which contains glycerol, alcohol, and catalyst.

g. Optionally, a continuous centrifuge (2) at the top of the reactor.

h. The packed volume fraction in the reactor is between 2% and 50%.

i. The reactor temperature is kept constant between 25° C. and 180° C. depending on the alcohol that is used.

j. The molar ratio of alcohol to oil or fat is between 3:1 and 10:1 including the supply currents of alcohol, glycerol and the catalyst.

k. The catalyst can be any homogeneous alkaline catalyst that is used in alcoholysis, such as $CH_3ONa$, $CH_3OK$, NaOH, KOH, or their mixtures, with a weight proportion in the range from 0.5% and 3.0% with respect to the oil flow.

l. At least one feed of alcohol, glycerol and catalyst (21, 22, 23, 31, 32) must be located at a height h between 0% and 80% as measured from the top of the reactor (where h=0% is the top, and h=100% is the bottom of the reactor).

The alcoholysis reactions for obtaining fatty acid alkyl esters are based on the reactions of triglycerides with alcohol as shown below:

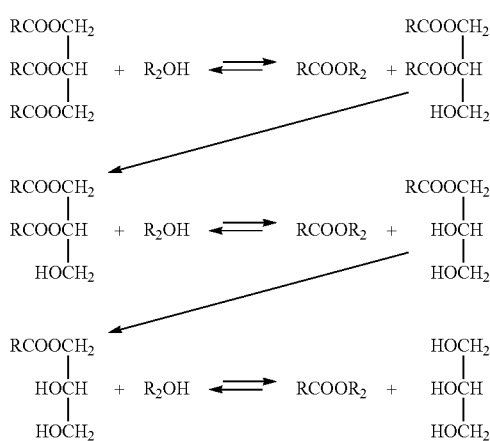

FIG. 2. Triglyceride alcoholysis.

Axially-aligned metallic threads with diameters between 0.05 mm and 3.00 mm are used for packing in the reaction system. Their contact area per unit packed volume is between 80,000 and 1,333 $m^2$ per $m^3$ of packing. However, other structured or semi-structured packings can be used if they allow a flow pattern that is similar to that described below. The packing volumetric fraction can vary up to 75%.

Taking into account the packing material, the operation of the reactor, and the flow regime, one of the phases flows over the packing, whereas the other flows on top of the first without dispersion. The mass transfer takes place in the following manner. The alcohol and the active catalyst species diffuse toward the oily phase, where the reaction preferentially occurs, although it also takes place at the interface and to a lower extent in the alcoholic phase. The glycerol that forms in the oily phase or at the interface diffuses toward the alcoholic phase, while the alkyl ester that forms in the alcoholic phase or at the interface diffuses toward the oily phase. Because of the reversibility of the reaction, the rapid separation of the glycerol in the oily phase, where most of the reaction takes place, shifts the reaction toward the products, which eliminates the need for a new reaction stage.

The conversion and yield of the liquid film reactor that is operated counter-current with a single reaction stage are greater than 99.7% and 99.9%, respectively. The separation of the reactor effluent phases, which is commonly carried out by decanting, is eliminated because most of it takes place simultaneously with the reaction. This increases the productivity of the process, which is of the order 1.8 $m^3$ of alkyl esters per hour per $m^3$ of reactor.

DESCRIPTION OF THE FIGURES

Figure 1:
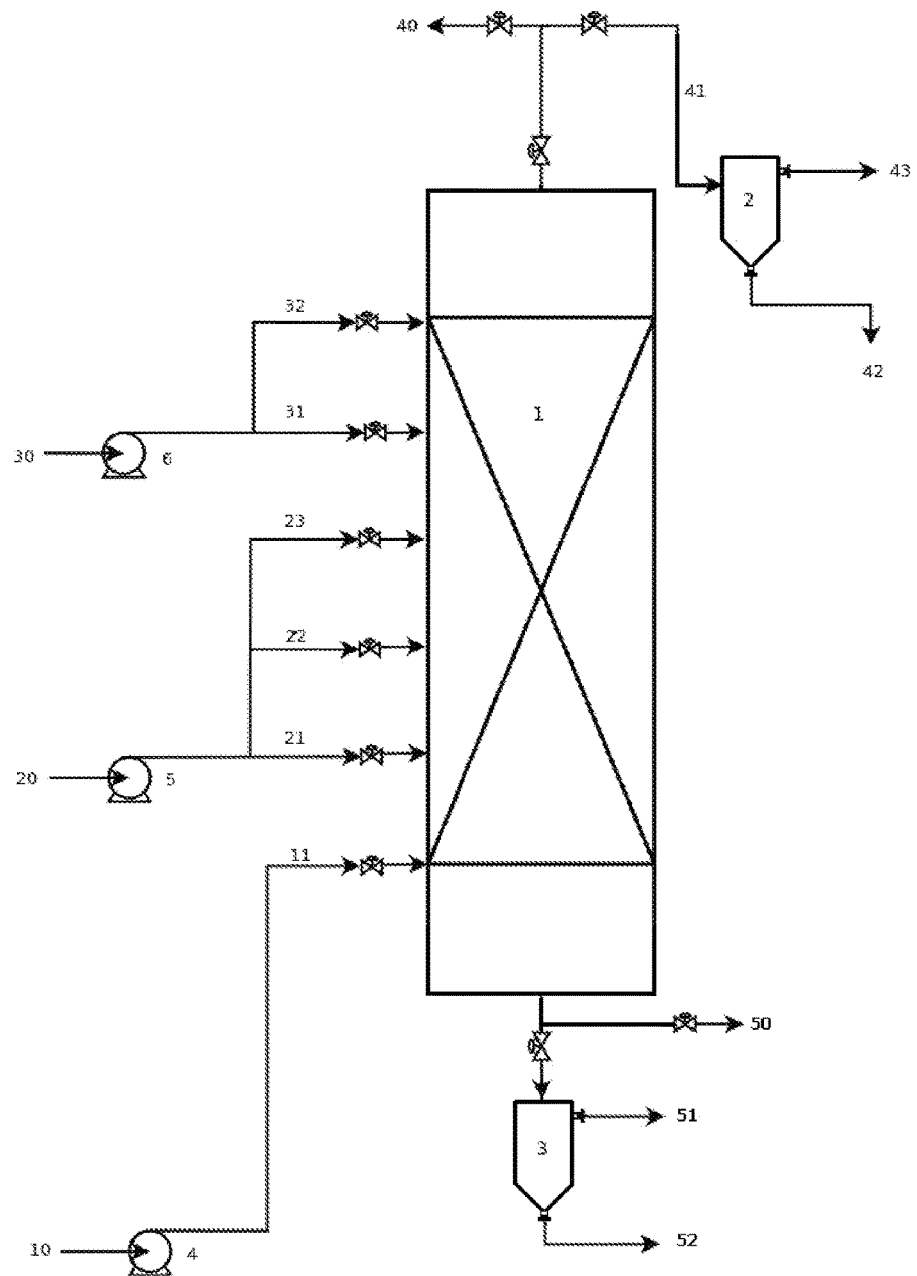
FIG. 1 depicts a schematic of the reaction system, including the liquid film reactor that is operated by counter-current.

FIG. 1 shows a preferred form of the proposed design (schematic of the reaction system, including the liquid film reactor that is operated counter-current):

The reactor is labeled with the number 1.

The pumps that are necessary for the process are labeled 4, 5 and 6.

The oil feed is labeled as 10. The oil input into the reactor corresponds to the current that is labeled as 11.

Current 20 corresponds to a mixture of alcohol, glycerol and catalyst that is fed to the intermediate region of reactor 1 in currents 21, 22 and 23. Current 20 will always be present and will be fed preferably at a height h between 0% and 80%, as measured from the top of the reactor such that h=0% corresponds to the top of reactor 1, and h=100% corresponds to the bottom.

Current 30, which is optional, is a mixture of alcohol, glycerol and catalyst that is fed to the intermediate region of reactor 1 in current 31, 32, or both currents 31 and 32.

The mixture of fatty acid alkyl esters, alcohol and catalyst is removed from the reactor through current 40 or may be subjected to additional separation in centrifuge 2, from which a current that is rich in fatty acid alkyl esters (43) and another that contains the remaining glycerol (42) are obtained.

The reactor has an outlet at its bottom from which a current (50) that contains glycerol, alcohol and catalyst is extracted. Centrifuge 3 can be used to provide additional separation of a rich phase in fatty acid alkyl esters (51) that could be dragged by the glycerol-rich phase (52).

Figure 2:
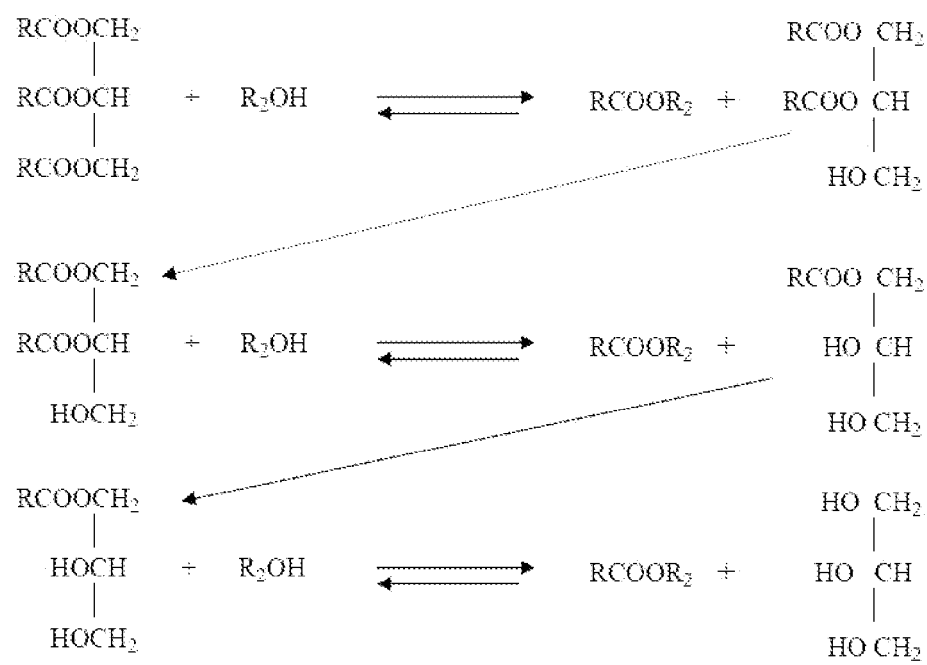
FIG. 2 shows the reaction of triglycerides with alcohol for obtaining fatty acid alkyl esters.

FIG. 2 shows the reaction of triglycerides with alcohol for obtaining fatty acid alkyl esters.

Figure 3:
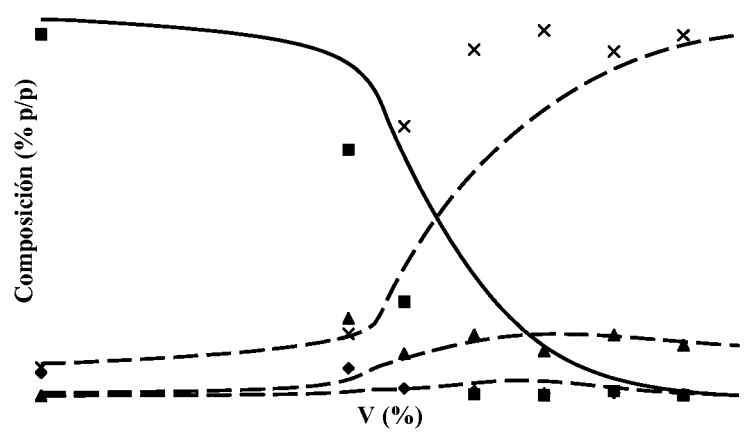
FIG. 3 is a first example of the application of the reaction system that shows data corresponding to experimental test 1CC.

FIG. 3 shows an example of the application of this reaction system. The data correspond to experimental test 1CC, the conditions of which are described in Table 1 (Profiles of the composition of a phase that is rich in methyl esters in the palm oil methanolysis in a liquid film reactor that is operated counter-current. The data correspond to reaction 1CC, and the tests were carried out under the conditions that are described in Table 1. Experimental data: (■) EM (♦) MG (▲) DG (x) TG. Data obtained from the model: (——) EM, (- - -) MG, (-•-•) DG, (- - -) TG).

Figure 4:
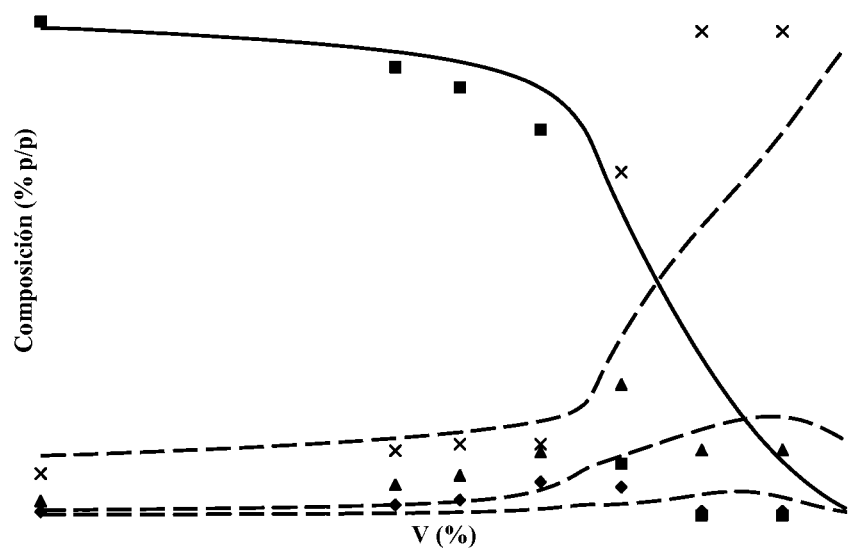
FIG. 4 is a second example of the application of the reaction system that shows data corresponding to experimental test 2CC.

FIG. 4 shows a second example of the application of this reaction system. The data correspond to experimental test 2CC, the conditions of which are described in Table 1 (Profiles of the composition of a phase that is rich in methyl esters in the palm oil methanolysis in a liquid film reactor that is operated counter-current. The data correspond to reaction 2CC, and the tests were carried out under the conditions that are described in Table 1. Experimental data: (■) EM (♦) MG (▲) DG (x) TG. Data obtained from the model: (——) EM, (- - -) MG, (-•-•) DG, (- - -) TG).

Figure 5:
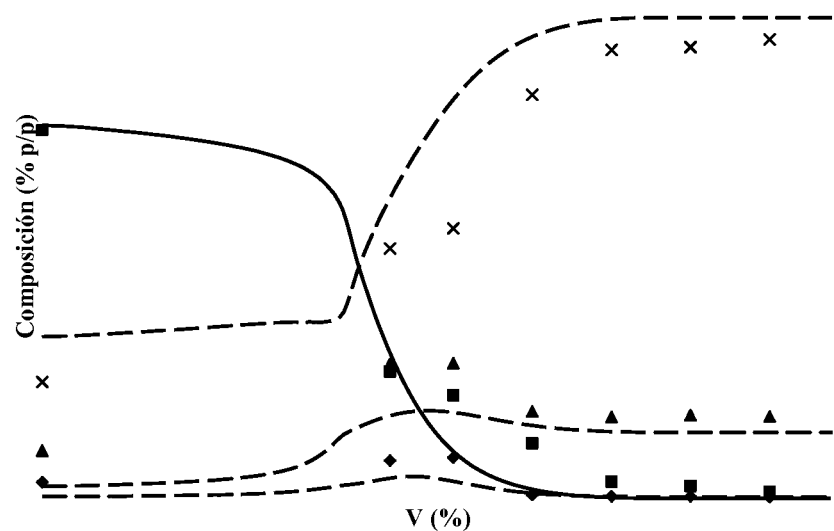
FIG. 5 is a third example of the application of the reaction system that shows data corresponding to experimental test 3CC.

FIG. 5 shows a third example of the application of the reactor system. The data correspond to experimental test 3CC, the conditions of which are described in Table 1 (Profiles of the composition of a phase that is rich in methyl esters in the palm oil methanolysis in a liquid film reactor that is operated counter-current. The data correspond to reaction 3CC, and the tests were carried out under the conditions described in Table 1. Experimental data: (■) EM (♦) MG (▲) DG (x) TG. Data obtained from the model: (———) EM, (- - -) MG, (-•-•) DG, (- - -) TG).

ILLUSTRATIVE EXAMPLES

Table 1 shows the conditions of some of the palm oil methanolysis processes that were carried out in a bench-scale liquid film reactor that operated counter-current with a maximum capacity of 5 kg/h of oil. All of the reactions took place at 60° C. using sodium hydroxide as a catalyst at a concentration of 1% w/w with respect to the feeding flow of palm oil. The profile of methyl esters, monoglycerides, diglycerides, triglycerides, and methanol was determined for each of the reactions.

TABLE 1

Experimental conditions of examples of the palm oil methanolysis process that was used for this patent.

| Reaction | Palm oil flow (g min$^{-1}$) | Methanol to palm oil molar ratio | Methanol feeding point (% V)$^a$ |
|---|---|---|---|
| 1CC | 32.8 | 5.8 | 47.7 |
| 2CC | 49.7 | 5.5 | 67.1 |
| 3CC | 32.9 | 5.7 | 38.0 |

$^a$Percentage of the total reactor volume measured from the top of the reactor.

FIGS. 3 through 5 show the concentration profiles that were obtained experimentally and those that were calculated using a model that was developed, fitted, and experimentally and statistically validated to simulate the behavior of the liquid film reactor that is operated counter-current, which is described in detail by Cadavid (2011).

Table 2 presents the compositions of the currents that are rich in fatty acid methyl esters and glycerol, which make up the effluent from the liquid film reactor that was operated counter-current with a maximum capacity of 5 kg/h of oil, for the operating conditions described below for palm oil methanolysis. The conversion was 99.7%, the yield was 99.9%, and the productivity was 1.8 m$^3$ FAME h$^{-1}$ m$^{-3}$.

The operating conditions were as follows:

| Temperature | 60° C. |
|---|---|
| Catalyst | NaOH |
| Catalyst concentration | 1% by weight with respect to the oil |
| Palm oil flow: | 50.0 g min$^{-1}$ |
| Methanol to palm oil molar ratio: | 8.0 gmol gmol$^{-1}$ |
| Methanol fraction through feed 1: | 1.00 |
| Feed point 1: | 76% |
| Glycerol weight fraction at feed 1: | 0.00 |

TABLE 2

Current compositions obtained from palm oil methanolysis in the liquid film reactor that was operated counter-current (w/w percentage).

| Compound | Current rich in fatty acid methyl esters (40 in FIG. 1) | Current rich in glycerol (50 in FIG. 1) |
|---|---|---|
| Methanol (M) | 15.40 | 5.84 |
| Fatty acid methyl ester (FAME) | 84.30 | 0.00 |
| Glycerol (G) | 0.00 | 93.71 |
| Triglycerides (TG) | 0.26 | 0.00 |
| Diglycerides (DG) | 0.04 | 0.00 |
| Monoglycerides (MG) | 0.01 | 0.44 |

Table 3 presents the compositions of the currents that are rich in fatty acid ethyl esters and in glycerol, which make up the effluent from the liquid film reactor that was operated counter-current with a maximum capacity of 5 kg/h of oil, for the operating conditions described below for the ethanolysis of soya bean oil. The conversion was 99.0%, the yield 99.9%, and the productivity was 1.1 m$^3$ FAEE h$^{-1}$ m$^{-3}$. The operating conditions were as follows:

| Temperature | 60° C. |
|---|---|
| Catalyst | NaOH |
| Catalyst concentration | 1% by weight with respect to the oil |
| Soy oil flow: | 30.0 g min$^{-1}$ |
| Ethanol to soya bean oil molar ratio: | 7.0 gmol gmol$^{-1}$ |
| Ethanol fraction through feed 1: | 1.00 |
| Feed point 1: | 76% |
| Glycerol weight fraction at feed 1: | 0.00 |

TABLE 3

Current compositions obtained from soya bean oil ethanolysis in the liquid film reactor that was operated counter-current (w/w percentage).

| Compound | Current rich in fatty acid ethyl esters (40 in FIG. 1) | Current rich in glycerol (50 in FIG. 1) |
|---|---|---|
| Ethanol (M) | 17.21 | 3.84 |
| Fatty acid ethyl esters (FAEE) | 81.90 | 0.00 |
| Glycerol (G) | 0.00 | 96.16 |
| Triglycerides (TG) | 0.78 | 0.00 |
| Diglycerides (DG) | 0.09 | 0.00 |
| Monoglycerides (MG) | 0.02 | 0.00 |

The invention claimed is:

1. A reactor system for the production of fatty acid alkyl esters by the alcoholysis of oils and fats, operated counter-current, comprising
    a. a falling liquid film reactor that is packed with metallic fibers with diameters between 0.05 mm and 3.00 mm or another type of packing that allows the formation of an interfacial area;
    b. an oil supply current that feeds the bottom of the reactor;
    c. a first supply current of a mixture that contains alcohol, glycerol and a catalyst that can feed any intermediate stage of the reactor;
    d. an optional second supply current of a mixture that contains alcohol, glycerol and the catalyst in different proportions than those in the first current that can feed any intermediate stage of the reactor or the top of the reactor, wherein the second current is always fed into the reactor above the feed(s) of the first current;
    e. an outlet at the top of the reactor through which flows a mixture of fatty acid alkyl esters, alcohol and the catalyst;

f. an outlet at the bottom of the reactor through which flows a mixture of glycerol, alcohol and the catalyst;
g. an optional continuous centrifuge for the separation of the remaining glycerol in the reactor's output current, which is rich in fatty acid alkyl esters;
h. an optional continuous centrifuge for the separation of the fatty acid alkyl esters that may have been dragged by the output current that is rich in glycerol;
i. the packed volume fraction in the reactor is between 2% and 75%;
j. the reactor temperature that is held constant between 25° C. and 180° C. depending on the alcohol that is employed;
k. an alcohol to oil molar ratio between 3:1 and 10:1 including the alcohol in any of the supply currents that contain mixtures of alcohol, glycerin and the catalyst;
l. the catalyst that is chosen from all homogeneous basic catalysts or their mixtures at a weight concentration between 0.5% and 3% with respect to the oil flow; and
m. wherein the reactor system operates counter-current with a feed of alcohol, glycerol and the catalyst located at a height h between 0% and 80% as measured from the top of the reactor such that h=0% is the top and h=100% is the bottom.

2. The reactor system for the production of fatty acid alkyl esters of claim 1 wherein the oil of the oil supply current is palm oil and the alcohol is methanol.

3. The reactor system for the production of fatty acid alkyl esters of claim 1 wherein the oil of the oil supply current is soybean oil and the alcohol is ethanol.

4. The reactor system for the production of fatty acid alkyl esters of claim 2 further comprising two feeds for the mixture of alcohol, glycerol and the catalyst at heights of 28.4% and 36.4% (where h=0% is the top of the reactor and h=100% is the bottom of the reactor).

5. The reactor system for the production of fatty acid alkyl esters of claim 3 further comprising two feeds for the mixture of alcohol, glycerol and the catalyst at heights of 28.4% and 34.8% (where h=0% is the top of the reactor and h=100% is the bottom of the reactor).

6. The reactor system for the production of fatty acid alkyl esters of claim 1 further comprising a packed volume fraction of 20%.

7. The reactor system for the production of fatty acid alkyl esters of claim 1 further comprising a packed volume fraction between 5% and 15%.

8. The reactor system for the production of fatty acid alkyl esters of claim 1 further comprising a Reynolds number inside of the reactor that is less than 4,000.

9. The reactor system for the production of fatty acid alkyl esters of claim 1 further comprising a Reynolds number inside of the reactor that is less than 3,000.

10. The reactor system for the production of fatty acid alkyl esters of claim 1 further comprising a Reynolds number inside of the reactor that is less than 2,400.

11. The reactor system for the production of fatty acid alkyl esters of claim 1 further comprising residence times inside of the reactor of between 2 and 30 minutes for oil or fat and between 3 and 60 minutes for the alcoholic phase for a conversion greater than 99% and a yield higher than 99%.

12. The reactor system for the production of fatty acid alkyl esters of claim 1 wherein the homogenous basic catalyst is selected from $CH_3ONa$, $CH_3OK$ NaOH, and KOH.

* * * * *